US012784197B2

(12) United States Patent
Taguchi et al.

(10) Patent No.: US 12,784,197 B2
(45) Date of Patent: Nov. 3, 2026

(54) MEDICAL IMAGE DIAGNOSIS SYSTEM AND TISSUE CHARACTERISTIC ESTIMATION METHOD

(71) Applicant: Canon Kabushiki Kaisha, Tokyo (JP)

(72) Inventors: Hiroki Taguchi, Otawara (JP); Shinsuke Tsukagoshi, Nasushiobara (JP); Yohei Minatoya, Tokyo (JP); Ryo Okuda, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 311 days.

(21) Appl. No.: 18/463,378

(22) Filed: Sep. 8, 2023

(65) Prior Publication Data

US 2024/0087119 A1 Mar. 14, 2024

(30) Foreign Application Priority Data

Sep. 9, 2022 (JP) ................................. 2022-143797

(51) Int. Cl.
*G06T 7/00* (2017.01)
*G06T 12/00* (2026.01)
(Continued)

(52) U.S. Cl.
CPC ............ *G06T 7/0012* (2013.01); *G06T 12/00* (2026.01); *G06V 10/764* (2022.01); *G16H 20/10* (2018.01);
(Continued)

(58) Field of Classification Search
CPC ....... A61B 5/055; A61B 6/481; A61B 5/0071; A61B 6/5247; A61B 6/00; A61B 8/481;
(Continued)

(56) References Cited

U.S. PATENT DOCUMENTS 8,606,349 B2 * 12/2013 Rousso ................. G01T 1/1642 424/9.1
10,206,643 B2 2/2019 Yamagata
(Continued)

FOREIGN PATENT DOCUMENTS

JP 2015-33578 A 2/2015
JP 2015-43975 A 3/2015
(Continued)

OTHER PUBLICATIONS

Office Action mailed Jun. 16, 2026, in Japanese Application No. 2022-143797 filed Sep. 9, 2022 w/partial English translation.

*Primary Examiner* — Courtney Joan Nelson
(74) *Attorney, Agent, or Firm* — Oblon, McClelland, Maier & Neustadt, L.L.P.

(57) ABSTRACT

A medical image diagnosis system includes an imaging apparatus and processing circuitry. The imaging apparatus applies one-time or multiple-time medical imaging to a subject to which a plurality of drugs having a tissue accumulation property, which corresponds to a tissue characteristic, are administered successively or simultaneously. The processing circuitry reconstructs one or a plurality of medical images, based on one or a plurality of set of raw data acquired by the one-time or multiple-time medical imaging. The processing circuitry estimates a tissue characteristic of a target region, based on a spatial distribution of the drugs rendered on the one or the plurality of medical images. The processing circuitry displays the estimated tissue characteristic.

11 Claims, 10 Drawing Sheets

(51) Int. Cl.

| | |
|---|---|
| ***G06V 10/764*** | (2022.01) |
| ***G16H 20/10*** | (2018.01) |
| ***G16H 50/20*** | (2018.01) |

(52) U.S. Cl.
CPC ... *G16H 50/20* (2018.01); *G06T 2207/10104* (2013.01); *G06T 2207/30096* (2013.01)

(58) Field of Classification Search
CPC ..... A61B 6/484; A61B 5/4848; A61B 6/5205; A61B 6/5217; A61B 8/5223; A61B 6/4417; A61B 6/463; A61B 6/54; A61B 5/0013; A61B 5/0035; A61B 5/0075; G06T 7/0012; G06T 2207/30004; G06T 11/003; G06T 2207/30096; G06T 2207/30104; G06T 7/00; G06T 2207/10096; G06T 2207/10104; G06V 2201/03; G06V 10/764; G16H 50/20; G16H 20/10
See application file for complete search history.

(56) References Cited

U.S. PATENT DOCUMENTS

| | | | | |
|---|---|---|---|---|
| 10,806,419 | B2 | 10/2020 | Tsuyuki et al. | |
| 11,246,877 | B2 | 2/2022 | Lin et al. | |
| 2006/0052690 | A1 * | 3/2006 | Sirohey .................. | A61B 6/481 600/420 |
| 2008/0033291 | A1 | 2/2008 | Rousso et al. | |
| 2010/0080757 | A1 * | 4/2010 | Haaga .................... | A61B 5/411 424/9.4 |
| 2015/0221082 | A1 * | 8/2015 | Carmi .................. | A61B 8/5223 382/128 |
| 2023/0284994 | A1 * | 9/2023 | Stransky-Heilkron ...................... | A61B 6/032 |

FOREIGN PATENT DOCUMENTS

| | | | | |
|---|---|---|---|---|
| JP | 2015-524329 | 8/2015 | | |
| JP | 2019-523757 A | 8/2019 | | |
| WO | WO-2022008374 A1 * | 1/2022 | ........... | G06F 18/253 |

* cited by examiner

MEDICAL IMAGE DIAGNOSIS SYSTEM AND TISSUE CHARACTERISTIC ESTIMATION METHOD

CROSS-REFERENCE TO RELATED APPLICATION

This application is based upon and claims the benefit of priority from prior Japanese Patent Application No. 2022-143797, filed Sep. 9, 2022, the entire contents of which are incorporated herein by reference.

FIELD

Embodiments described herein relate generally to a medical image diagnosis system and a tissue characteristic estimation method.

BACKGROUND

In peripheral blood vessels or new feeding vessels of cancer cells that have progressed to some extent, an EPR (enhanced permeability and retention) effect occurs. The EPR effect is such a phenomenon that there occur an enhancement in vascular permeability due to dilation of gaps between vascular endothelial cells, and an enhancement in accumulation of a vascular permeant substance due to lymphatic system underdevelopment. It is known that the vascular endothelial cell gap is about 5 to 50 nm in normal cells, and is about 100 to 200 nm or more at a time when the EPR effect occurs.

A DDS (drug delivery system) utilizing the EPR effect has been devised. In the DDS utilizing the EPR effect, nanoparticles are processed or a drug is sealed by using a liposome or the like, thereby controlling the particle size to a several-hundred nm size, and drug particles are delivered to a cancer tissue. It is assumed that the particle size of drug particles to be delivered to a cancer tissue, the kind of drug, and so forth vary in accordance with a tumor characteristic such as a progress degree, type, or the like of cancer, but there is no method of appropriately determine these.

DETAILED DESCRIPTION

According to one embodiment, a medical image diagnosis system includes an imaging unit, a reconstruction unit, an estimation unit and a display control unit. The imaging unit applies one-time or multiple-time medical imaging to a subject to which a plurality of drugs having a tissue accumulation property, which corresponds to a tissue characteristic, are administered successively or simultaneously. The reconstruction unit reconstructs one or a plurality of medical images, based on one or a plurality of set of raw data acquired by the one-time or multiple-time medical imaging. The estimation unit estimates a tissue characteristic of a target region included in the subject, based on a spatial distribution of the drugs rendered on the one or the plurality of medical images. The display control unit displays the estimated tissue characteristic on a display device.

Hereinafter, referring to the accompanying drawings, embodiments of a medical image diagnosis system and a tissue characteristic estimation method are described in detail.

First Embodiment

Figure 1:
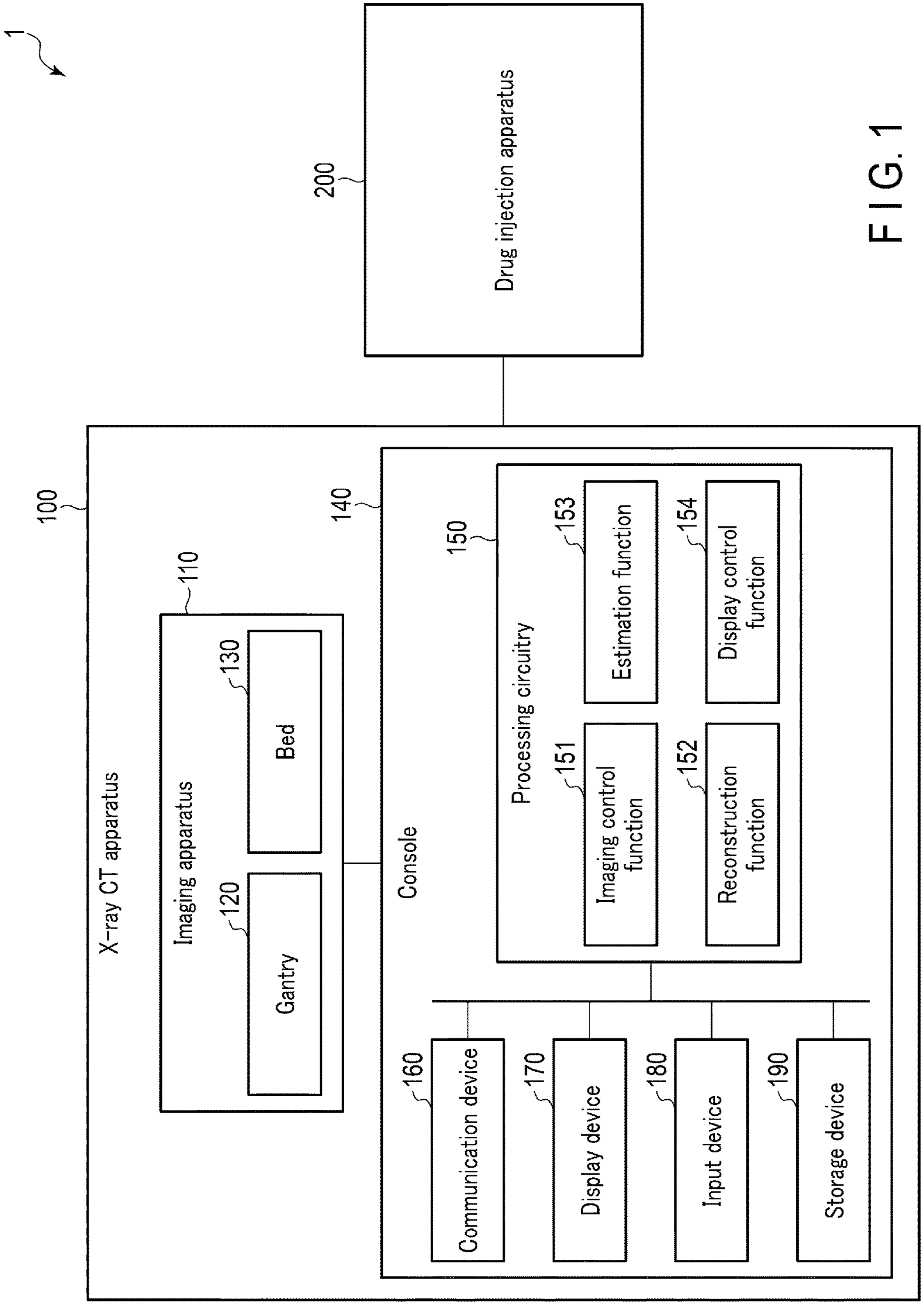
FIG. 1 is a diagram illustrating a configuration example of a medical image diagnosis system according to a first embodiment.

FIG. 1 is a diagram illustrating a configuration example of a medical image diagnosis system 1 according to a first embodiment. As illustrated in FIG. 1, the medical image diagnosis system 1 is a computer network including an X-ray CT apparatus (X-ray computed tomography apparatus) 100 and a drug injection apparatus 200. The X-ray CT apparatus 100 and the drug injection apparatus 200 are connected to be capable of mutually communicating information.

As illustrated in FIG. 1, the X-ray CT apparatus 100 includes an imaging apparatus 110 and a console 140, which are connected to be capable of mutually communicating information. The imaging apparatus 110 is a machinery apparatus for executing X-ray CT imaging on a subject. The X-ray CT imaging according to the present embodiment is applicable to any of single energy CT (SECT), dual energy CT (DECT) and photon counting CT (PCCT), but in the description below the photon counting CT (PCCT) is assumed.

The imaging apparatus 110 includes a gantry 120 and a bed 130. The gantry 120 is a substantially cylindrical machinery structure including an opening that forms an imaging space. The gantry 120 includes, in a housing, a rotating frame having a substantially cylindrical shape and a stationary frame that supports the rotating frame such that the rotating frame is rotatable around a rotational axis. Specifically, the stationary frame rotatably supports the rotating frame via a slip ring. In the rotating frame, an X-ray generating device and an X-ray detection device are attached to the rotating frame such that the X-ray generating device and X-ray detection device are opposed to each other, with the rotational axis being interposed.

The X-ray generating device includes an X-ray tube and a high-voltage generator. The X-ray tube generates X-rays in accordance with the control of tube voltage and tube current by the high-voltage generator. The X-ray detection device includes an X-ray detector and data collection circuitry. The X-ray detector detects X-rays that are generated from the X-ray tube and pass through the subject. In one example, the X-ray detector includes a plurality of semiconductor detection elements formed by compound semiconductors or the like, which are densely arranged in a two-dimensional fashion with respect to a channel direction and a column direction. The semiconductor detection elements capture incident X-ray photons, and convert the X-ray photons into an electric signal having an electric charge corresponding to the energy of the X-ray photons. The data collection circuitry counts X-ray photons, based on the electric signal. In one example, the data collection circuitry counts, by a pulse-height discriminator, the number of X-ray photons in regard to each of a plurality of bins, and collects spectral data representing a distribution of the number (count number) of X-ray photons over the bins. To be more specific, the spectral data is collected in regard to each of views, which mean data sampling points with respect to the X-ray tube rotational direction. Note that the bin means an energy band. The spectral data is transmitted to the console.

The bed 130 includes a table top on which the subject is placed, and a base that movably supports the table top. The subject and the table top are positioned such that a to-be-imaged region of the subject is positioned in the imaging space. Note that the to-be-imaged region according to the present embodiment may be any region if the region includes a tumor, such as a chest part, a waist part, a leg part, an arm part, or a head part. The present embodiment is applicable to both of a benign tumor and a malignant tumor. The malignant tumors can be classified into a carcinoma (malignant epithelial tumor) and a sarcoma (malignant non-epithelial tumor), and the present embodiment is applicable to both malignant tumors. In the description below, it is assumed that the tumor is cancer that is a malignant tumor.

Figure 2:
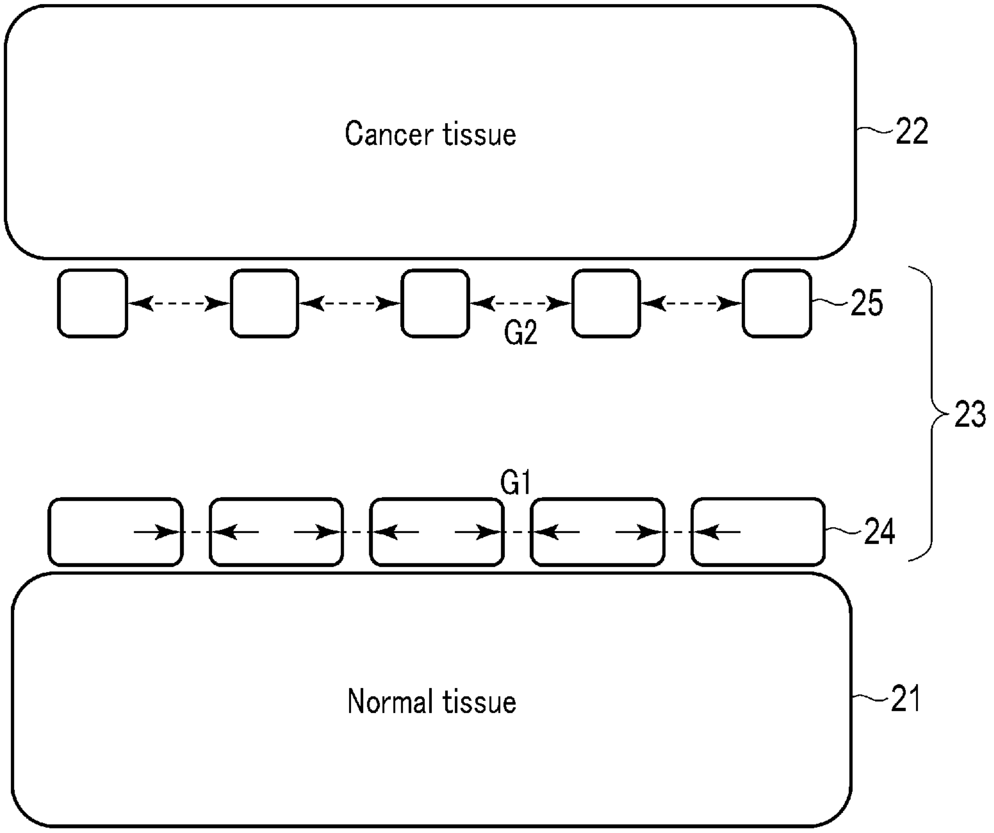
FIG. 2 is a diagram illustrating a structure example of a blood vessel that feeds a cancer tissue.

FIG. 2 is a diagram illustrating a structure example of a blood vessel that feeds a cancer tissue. FIG. 2 exemplarily illustrates a normal tissue 21 that is a tissue in which no cancer occurs, and a cancer tissue 22 that is a tissue in which cancer occurs. The normal tissue 21 and cancer tissue 22 are fed by a blood vessel 23. A vessel wall of the blood vessel 23 is composed of vascular endothelial cells 24, 25. Gaps are provided between the vascular endothelial cells 24, 25, and nutritional components or the like flowing in the blood vessel 23 pass through the gaps and are fed to the normal tissue 21 and cancer tissue 22 via interstitial fluid.

With the progress of cancer, the EPR effect occurs in a peripheral blood vessel or new feeding vessel of the cancer tissue 22, the vascular endothelial cells 25 contract, and gaps G2 between the vascular endothelial cells 25 dilate. As illustrated in FIG. 2, a gap G1 between the vascular endothelial cells 24 occupied by the normal tissue 21 is typically about 5 to 50 nm. However, the gap G2 of the vascular endothelial cells 25, in which the EPR effect occurs, is greater than the gap G1, and dilates to about 150 nm or more. Note that in the description below, the gap between vascular endothelial cells is also referred to simply as “gap”.

The imaging apparatus 110 executes PCCT imaging on the subject in accordance with the control by the console 140. A plurality of drugs having a tumor accumulation property, which corresponds to a tumor characteristic, are administered successively or simultaneously to the subject. The tumor characteristic means the progress degree or type of a tumor. The tumor accumulation property means a capability of accumulation of a drug in a tumor. The imaging apparatus 110 applies one-time or multiple-time PCCT imaging to the subject to which drugs having a tumor accumulation property, which corresponds to a tumor characteristic, are administered successively or simultaneously, and collects one or a plurality of spectral data that are collected by the one-time or multiple-time medical imaging. If a plurality of drugs can be distinguished and visualized by one-time PCCT imaging, it suffices that the PCCT imaging is executed only once. If a plurality of drugs cannot be distinguished and visualized by one-time PCCT imaging, the PCCT imaging needs to be executed multiple times.

It is assumed that the tumor characteristic according to the first embodiment is a progress degree for evaluating the degree of progress of cancer. In one example, the progress degree can be expressed by a TNM classification, a stage of disease, or the like. The TNM classification is defined by a combination of factors of a size (T) of a tumor, a degree (N) of metastasis of a lymph node, and a degree (M) of remote metastasis to other regions. The combination of the factors corresponds to the stage of disease. The progress degree may be defined by the size (T) of a tumor, the degree (N) of metastasis of a lymph node, or the degree (M) of remote metastasis to other regions, or some other freely selected index may be used. In the present embodiment, it is assumed that the gap dilates in accordance with the progress degree. In the first embodiment, a plurality of drugs having different particle sizes are injected into the subject. The progress degree of a target cancer tissue is estimated based on a spatial distribution of the drugs in a target region. In the description below, it is assumed that the progress degree is the stage of disease.

Figure 3:
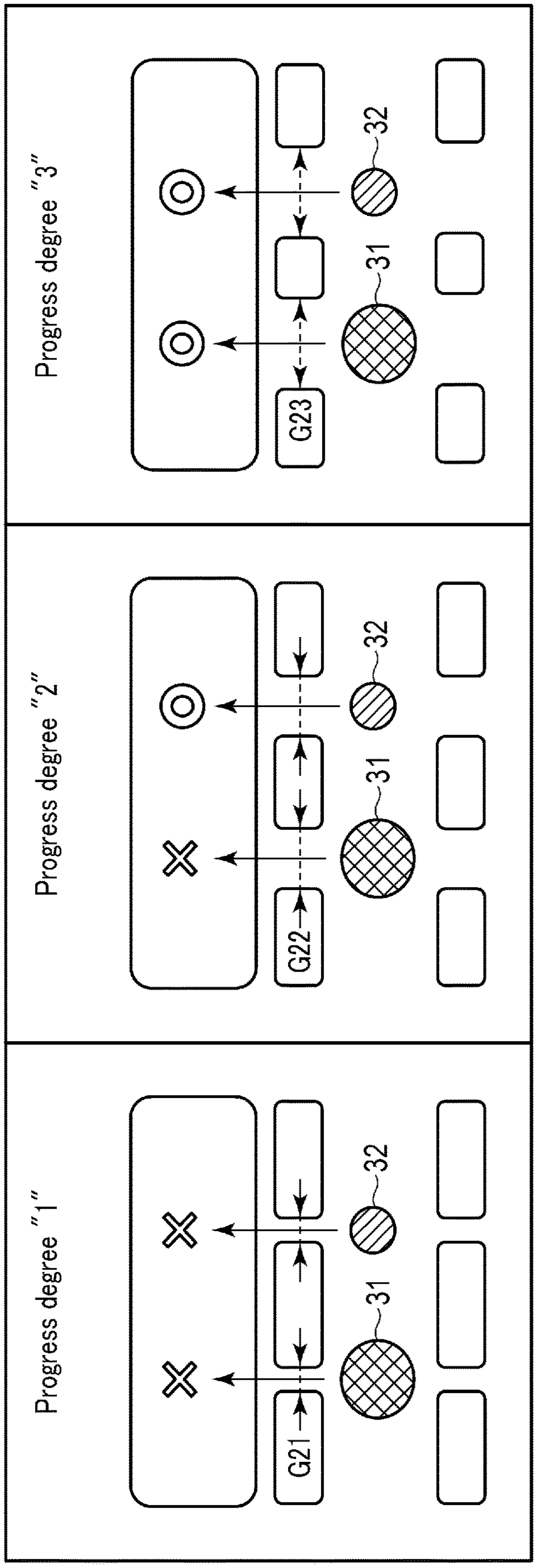
FIG. 3 is a diagram representing a relationship between a progress degree and a gap between vascular endothelial cells.

FIG. 3 is a diagram representing a relationship between the progress degree and the gap. In FIG. 3, it is assumed that a drug particle 31 with a relatively large particle size and a drug particle 32 with a relatively small particle size are injected in the subject. It is assumed that cancer deteriorates as a value of the progress degree becomes greater. In a case of a progress degree “1”, a gap G21 is relatively narrow, and neither the drug particle 31 nor the drug particle 32 cannot pass through the gap G21. In a case of a progress degree “2”, a gap G22 is wider than the gap G21, and the drug particle 32 can pass through the gap G22, although the drug particle 31 cannot pass through the gap G22. In a case of a progress degree “3”, a gap G23 is further wider than the gap G22, and each of the drug particle 31 and drug particle 32 can pass through the gap G23.

In other words, in a case where neither the drug particle 31 nor the drug particle 32 is distributed in the cancer tissue, this means that the progress degree is “1”; in a case where the drug particle 31 is not distributed in the cancer tissue but the drug particle 32 is distributed in the cancer tissue, this means that the progress degree is “2”; and in a case where both the drug particle 31 and the drug particle 32 are distributed in the cancer tissue, this means that the progress degree is “3”. In this manner, in the case where the tumor characteristic is the progress degree, the tumor accumulation property means the ease of accumulation in a tumor, which corresponds to the particle size of the drug.

The drug according to the present embodiment may be of any kind, if the drug can be visualized by PCCT imaging. Specifically, a contrast agent that can be visualized by PCCT imaging may be used, or a drug, in which a curative medicine for a cancer tissue, such as an anticancer drug, is labeled with a high atomic number substance, may be used.

As the high atomic number substance, a freely selected heavy metal, such as gold, silver or platinum, may be used.

The console 140 is a computer that controls the imaging apparatus 110. The console 140 includes processing circuitry 150, a communication device 160, a display device 170, an input device 180 and a storage device 190. The processing circuitry 150, communication device 160, display device 170, input device 180 and storage device 190 are connected to be capable of mutually communicating information.

The processing circuitry 150 includes a processor such as a CPU (Central Processing Unit). The processor starts a tumor characteristic estimation program that is installed in the storage device 190 or the like, thereby implementing an imaging control function 151, a reconstruction function 152, an estimation function 153 and a display control function 154. The functions 151 to 154 may not necessarily be implemented by single processing circuitry. A plurality of independent processors may be combined to constitute processing circuitry, and the respective processors may implement the functions 151 to 154 by executing the tumor characteristic estimation program. In addition, the functions 151 to 154 may be implemented as modules constituting the tumor characteristic estimation program, or may be implemented as individual hardware.

By implementing the imaging control function 151, the processing circuitry 150 controls the various devices of the imaging apparatus 110 in accordance with an imaging sequence for PCCT imaging. The processing circuitry 150 controls the various devices of the imaging apparatus 110 in order to apply one-time or multiple-time PCCT imaging to a subject to which a plurality of drugs having a tumor accumulation property, which corresponds to a tumor characteristic, are administered successively or simultaneously. In accordance with the control by the processing circuitry 150, the imaging apparatus 110 executes one-time or multiple-time PCCT imaging on a to-be-imaged region of the subject, and collects one or a plurality of spectral data relating to the to-be-imaged region. Specifically, the drugs are labeled with mutually different high atomic number substances, and the processing circuitry 150 executes, as the one-time or multiple-time PCCT imaging, K-edge imaging and/or material decomposition using spectral analysis on targets that are high atomic number substances included in the respective drugs.

By implementing the reconstruction function 152, the processing circuitry 150 reconstructs one or a plurality of PCCT images, based on one or a plurality of spectral data collected by one-time or multiple-time PCCT imaging. A reconstruction algorithm is not particularly limited, and use can be made of, as appropriate, analytical reconstruction using FBP (filtered back projection), iterative approximation reconstruction that iteratively updates images in such a manner as to optimize an objective function in which various models are formulated, and machine learning reconstruction in which denoise processing by a neural network is assembled in the iterative approximation reconstruction.

By implementing the estimation function 153, the processing circuitry 150 estimates a tumor characteristic of a target region included in the subject, based on a spatial distribution of a plurality of drugs rendered on one or a plurality of PCCT images. The target region is a tumor, or a tissue that is suspected to be a tumor, which is a target of estimation of a tumor characteristic. As described above, in the first embodiment, the tumor characteristic is the progress degree. Specifically, the processing circuitry 150 estimates that the progress degree is a first progress degree in a case where only a drug of a first particle size, among a plurality of drugs, is distributed in the target region on one or a plurality of medical images, and estimates that the progress degree is a second progress degree that is more advanced than the first progress degree, in a case where a drug of a second particle size greater than the particle size of the first particle size, among the drugs, is distributed in the target region on one or a plurality of medical images. In addition, in a case where each of the drug of the first particle size and the drug of the second particle size is distributed in the target region, the processing circuitry 150 estimates that the progress degree is a third progress degree that is less advanced than the first progress degree.

By implementing the display control function 154, the processing circuitry 150 displays various information on the display device 170. In one example, the processing circuitry 150 displays the PCCT image, progress degree, and the like. In another example, the processing circuitry 150 visually distinguishably displays the drugs rendered on one or a plurality of PCCT images.

The communication device 160 is an interface for connection to the drug injection apparatus 200, a work station, a PACS (Picture Archiving and Communication System), a HIS (Hospital Information System), a RIS (Radiology Information System), or the like, via a LAN (Local Area Network) or the like. The communication device 160 transmits and receives various data to and from a connection destination.

The display device 170 displays various information in accordance with the display control function 154 of the processing circuitry 150. As the display device 170, use can be made of, as appropriate, a liquid crystal display (LCD), a cathode ray tube (CRT) display, an organic electro-luminescence (EL) display (OELD), a plasma display, or some other freely chosen display. Besides, the display device 170 may be a projector.

The input device 180 accepts various input operations from a user, converts an accepted input operation to an electric signal, and outputs the electric signal to the processing circuitry 150. Specifically, the input device 180 is connected to input devices such as a mouse, a keyboard, a trackball, a switch, a button, a joystick, a touchpad, and a touch panel display. The input device 180 outputs to the processing circuitry 150 an electric signal corresponding to an input operation to the input device 180. In addition, the input device 180 may be an input device provided in some other computer that is connected via a network or the like. The input device 180 may be a speech recognition device that converts a voice signal collected by a microphone into an instruction signal.

The storage device 190 is a storage device that stores various data, such as a ROM (Read Only Memory), a RAM (Random Access Memory), an HDD (Hard Disk Drive), an SSD (Solid State Drive), an integrated circuit storage device, or the like. The storage device 190 stores, for example, a treatment support program or the like. The storage device 190 may be, aside from the above-mentioned storage devices, a portable storage medium such as a CD (Compact Disc), a DVD (Digital Versatile Disc) or a flash memory, or a drive device that reads and writes various information from and to a semiconductor memory element or the like. The storage device 190 may be provided in some other computer that is connected to the X-ray CT apparatus 100 via a network.

The drug injection apparatus 200 is a machinery apparatus that injects a drug into a subject. Specifically, the drug injection apparatus 200 includes a cylinder that is a mechanism that discharges a drug, and control circuitry that controls the operation of the cylinder by motor driving. Note that the cylinder may be operated based on machine control by the control circuitry, or may be operated manually by a worker.

Next, a progress degree estimation process by the medical image diagnosis system 1.

Figure 4:
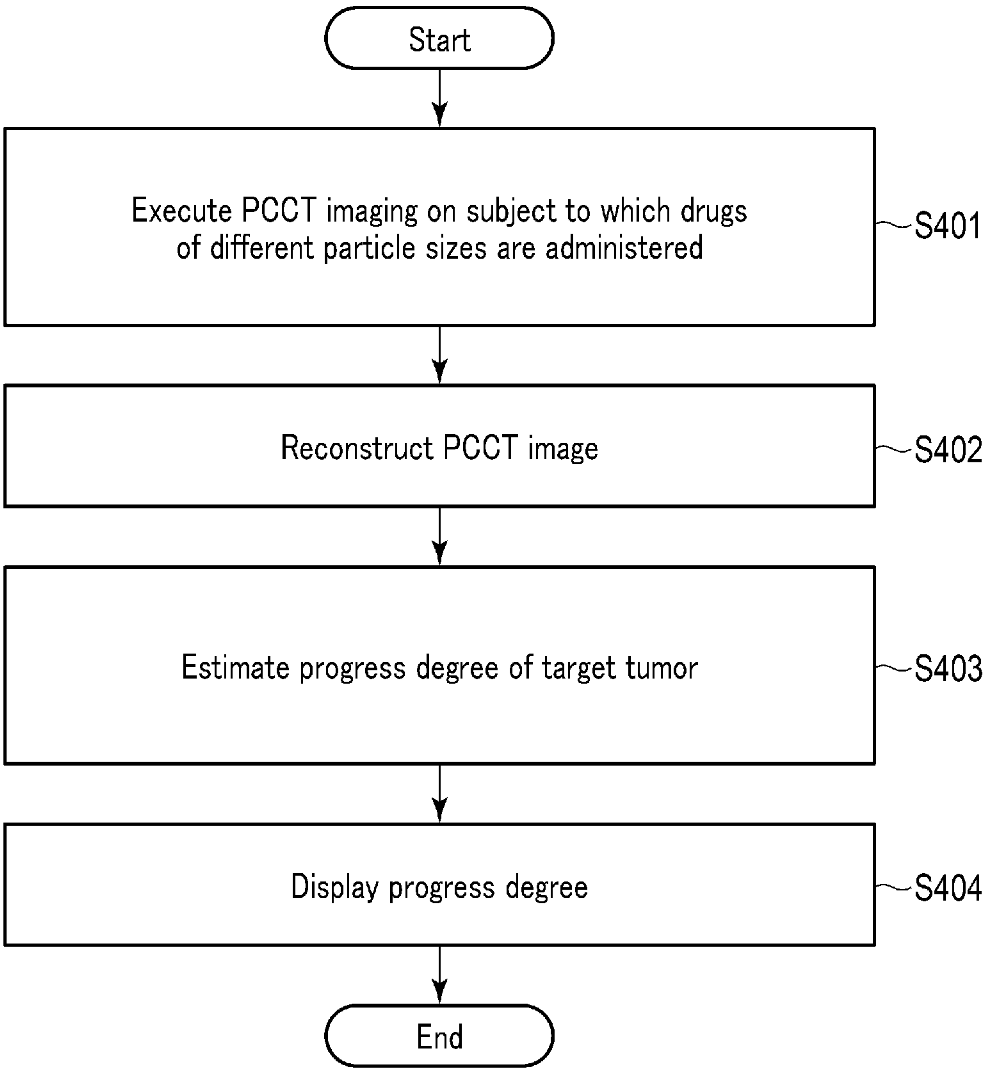
FIG. 4 is a flowchart illustrating a processing procedure relating to a progress degree estimation process according to the first embodiment.

FIG. 4 is a flowchart illustrating a processing procedure relating to the progress degree estimation process according to the first embodiment. FIG. 4 assumes such a scene that it is found that a target tumor, which is suspected to be cancer, is present in the subject, and the progress degree of the target tumor is specified by the present progress degree estimation process.

As illustrated in FIG. 4, by implementing the imaging control function 151, the processing circuitry 150 executes PCCT imaging on the subject to which a plurality of drugs with different particle sizes are administered (step S401). In step S401, the processing circuitry 150 controls various structural devices of the imaging apparatus 110, and applies one-time or multiple-time PCCT imaging to the subject to which a plurality of drugs having a tumor accumulation property, which corresponds to a tumor characteristic, are administered successively or simultaneously. The order of execution of drug injection and PCCT imaging is variable.

Figure 5:
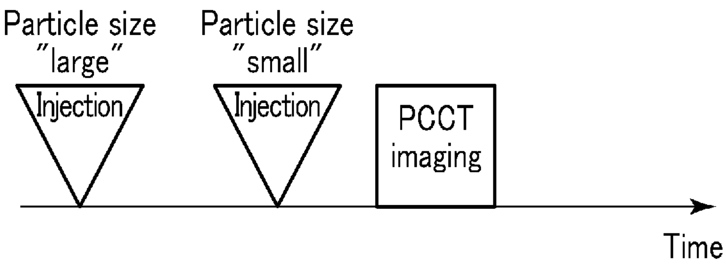
FIG. 5 is a timing chart of drug injection and PCCT imaging executed in step S401.

FIG. 5 is a timing chart of drug injection and PCCT imaging executed in step S401. In one example, it is assumed that drugs to be injected are a drug of a particle size "large" and a drug of a particle size "small". It is assumed that the drug of particle size "large" can be accumulated only in a cancer tissue of a progress degree "3", and the drug of particle size "small" can be accumulated in cancer tissues of progress degrees "3" and "2".

As illustrated in FIG. 5, to begin with, the drug injection apparatus 200 injects the drug of particle size "large". Thereafter, the drug injection apparatus 200 injects the drug of particle size "small". The injection of the drug of particle size "small" is executed before the drug of particle size "large", which is accumulated in the target tumor, is discharged or absorbed. The time from the injection of the drug of particle size "large" to the injection of the drug of particle size "small" is adjusted as appropriate, in accordance with the tumor characteristic of the target tumor, the kind of the injected drugs, and the like. Using the injection of the drug of particle size "small" as a trigger, the X-ray CT apparatus 100 executes PCCT imaging on the target tumor of the subject. Note that if it is confirmed that the drug of particle size "large" accumulates in the target tumor, the drug of particle size "small" may not be injected, for example, in order to reduce the load on the subject, and to shorten the processing time. Whether the drug of particle size "large" is accumulated may be determined by a worker observing the PCCT image, or by the processing circuitry 150 executing an image recognition process on the PCCT image.

Another order of execution may be an order of "injection of drug of particle size 'small'"→"injection of drug of particle size 'large'"→"PCCT imaging". If it is confirmed that the drug of particle size "small" does not accumulate in the target tumor, the drug of particle size "large" may not be injected, for example, in order to reduce the load on the subject, and to shorten the processing time. If the degree of interference between the drug of particle size "small" and the drug of particle size "large" can be ignored, the drug of particle size "small" and the drug of particle size "large" may be injected at the same time.

The drug of particle size "large" and the drug of particle size "small" are labeled with high atomic number substances with different K-edges, such that the drug of particle size "large" and the drug of particle size "small" can be distinguished on the PCCT image by K-edge imaging. To be more specific, it is assumed that the high atomic number substances of the drugs have different K-edges to such a degree that the high atomic number substances can be distinguished by the energy resolution of the X-ray detection device.

If step S401 is executed, the processing circuitry 150 reconstruct the PCCT image by implementing the reconstruction function 152 (step S402). The processing circuitry 150 executes the reconstruction of the PCCT image, each time the drug injection is performed. In step S402, the processing circuitry 150 generates the PCCT image relating to the target tumor, by applying the reconstruction process to the spectral data collected in each PCCT imaging. To be more specific, the processing circuitry 150 generates, based on spectral data of a bin to which the K-edge of the drug of particle size "large" belongs, a first PCCT image representing a spatial distribution of the count number of the bin, and generates, based on spectral data of a bin to which the K-edge of the drug of particle size "small" belongs, a second PCCT image representing a spatial distribution of the count number of the bin. The first PCCT image represents the spatial distribution of the drug of particle size "large", and the second PCCT image represents the spatial distribution of the drug of particle size "small". Then, the processing circuitry 150 composites the first PCCT image and the second PCCT image, and generates a composite image representing the spatial distribution of the drug of particle size "large" and the drug of particle size "small". It is preferable to allocate, to each of pixels of the composite image, a label representing the kind of the bin, to which the count number allocated to the pixel belongs, or presenting the kind of the drug corresponding to the bin. Here, the label corresponding to the drug of particle size "large" is referred to as "large drug label", and the label corresponding to the drug of particle size "small" is referred to as "small drug label".

If step S402 is executed, the processing circuitry 150 estimates the progress degree of the target tumor by implementing the estimation function 153 (step S403). In step S403, the processing circuitry 150 estimates the progress degree of the target tumor, based on the spatial distribution of the drugs included in the composite image reconstructed in step S402.

Figure 6:
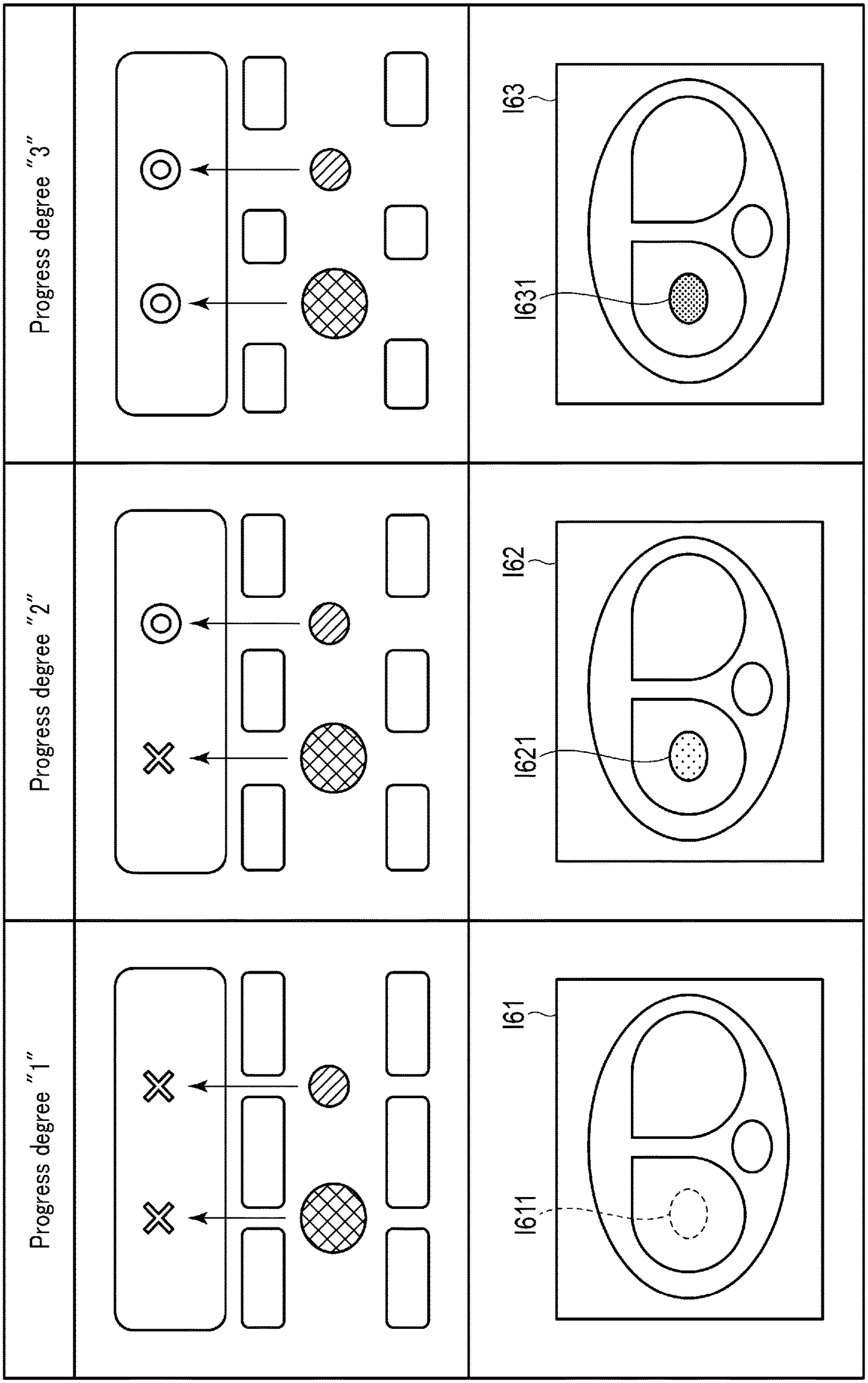
FIG. 6 is a diagram representing a relationship between a progress degree and a spatial distribution of a drug on a composite image.

FIG. 6 is a diagram representing a relationship between a progress degree and a spatial distribution of a drug on a composite image. The relationship between the progress degree and the gap between vascular endothelial cells is identical to the relationship illustrated in FIG. 3. As illustrated in a left column of FIG. 6, in the case of the progress degree "1", since each of both the drug of particle size "large" and the drug of particle size "small" does not pass through the gap, each of both drugs is not distributed in the target tumor. In this case, an image area of a target tumor (hereinafter "target tumor area") I611 included in a composite image I61 is not contrast-enhanced by both drugs. Specifically, in a case where each of both drugs is not distributed in the target tumor area I611, the processing circuitry 150 estimates that the progress degree is the progress degree "1".

As illustrated in a middle column of FIG. 6, in the case of the progress degree "2", since the drug of particle size "large" does not pass through the gap and the drug of particle size "small" passes through the gap, only the drug of particle size "small" is distributed in the target tumor. In this case, a target tumor area I621 included in a composite image I62 is contrast-enhanced by only the drug of particle size "small". Specifically, in a case where only the drug of particle size "small" is distributed in the target tumor area I621, the processing circuitry 150 estimates that the progress degree is the progress degree "2". As illustrated in a right column of FIG. 6, in the case of the progress degree "3", since both of the drug of particle size "large" and the drug of particle size "small" pass through the gap, both drugs are distributed in the target tumor. In this case, a target tumor area I631 included in a composite image I63 is contrast-enhanced by both drugs. Specifically, in a case where both drugs are distributed in the target tumor area I631, the processing circuitry 150 estimates that the progress degree is the progress degree "3".

In step S403, the processing circuitry 150 extracts the drug of particle size "large" and the drug of particle size "small" from the composite image. Specifically, the processing circuitry 150 can extract the drug of particle size "large" and the drug of particle size "small", based on the kind of the label allocated to each pixel. Then, if the drug of particle size "large" and the drug of particle size "small" are extracted, the progress degree "3" is estimated. If only the drug of particle size "small" is extracted, the progress degree "2" is estimated. If neither the drug of particle size "large" nor the drug of particle size "small" is extracted, the progress degree "1" is estimated. Whether the pixel of the processing target is the drug of particle size "large" or the drug of particle size "small" can be distinguished by the count number allocated to the pixel, or by the pin to which the count number belongs.

If step S403 is executed, the processing circuitry 150 displays the progress degree estimated in step S403, by implementing the display control function 154 (step S404). In step S404, the processing circuitry 150 displays the progress degree on the display device 170 with a freely selected layout.

Figure 7:
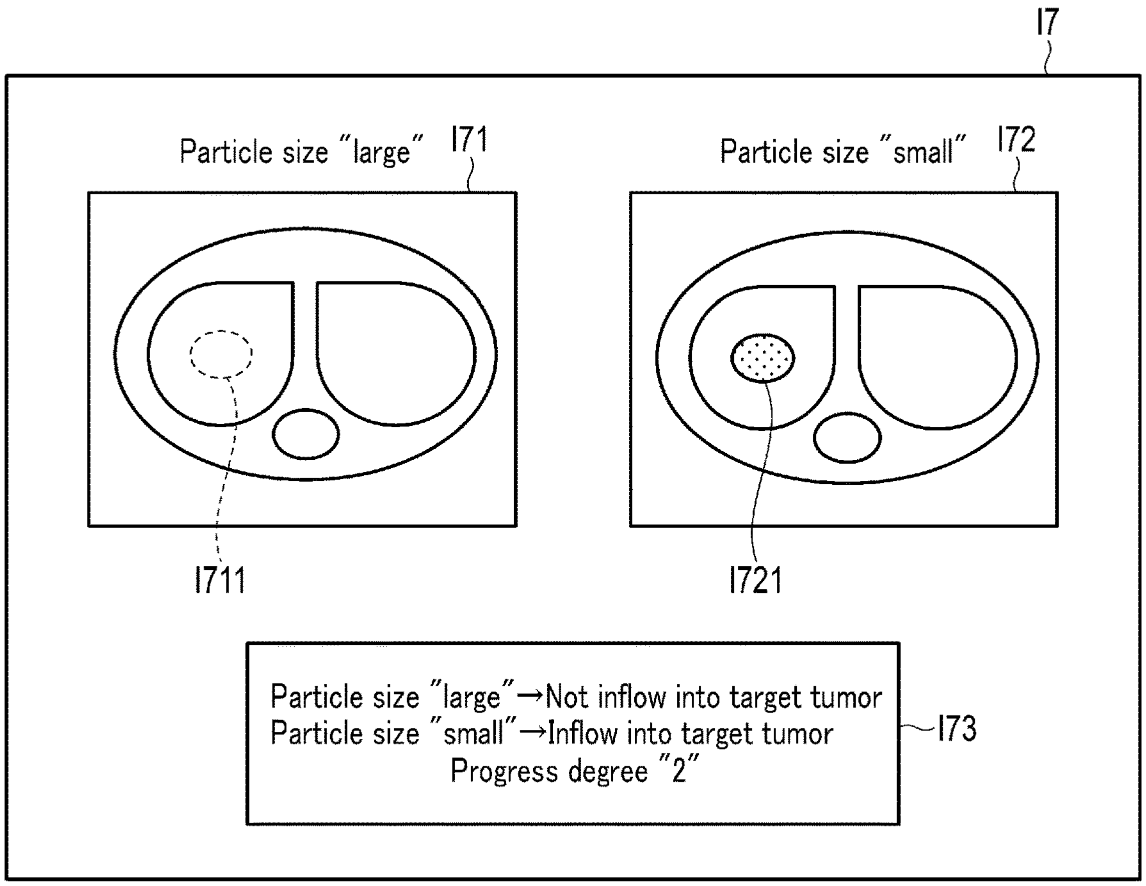
FIG. 7 is a diagram exemplarily illustrating a display screen of a progress degree.

FIG. 7 is a diagram exemplarily illustrating a display screen I7 of a progress degree. As illustrated in FIG. 7, the display screen I7 displays a PCCT image I71 corresponding to the drug of particle size "large", a PCCT image I72 corresponding to the drug of particle size "small", and a display field I73 of the progress degree. In one example, it is assumed that the drug of particle size "large" is not extracted in a target tumor I711 on the PCCT image I71, and the drug of particle size "small" is extracted in a target tumor I721 on the PCCT image I72. As illustrated in FIG. 6, the progress degree in this case is the progress degree "2". The display field I73 displays a message relating to the progress degree, which indicates that the progress degree is the progress degree "2". Note that it is preferable that the drug of particle size "large", which is extracted on the PCCT image I71, and the drug of the particle size "small", which is extracted on the PCCT image I72, are visually distinguishably displayed by colors or the like.

As illustrated in FIG. 7, since the progress degree and the PCCT images I71 and I72 are displayed in an arranged manner, the worker can evaluate the reliability of the progress degree by confirming the PCCT images I71 and I72. In addition, it is preferable that the presence or absence of entrance of each drug into the target tumor is displayed as grounds that the progress degree is "2". In the case of the above example, the grounds are displayed as "particle size 'large'→not inflow into target tumor", and "particle size 'small'→inflow into target tumor".

Note that the display screen I7 illustrated in FIG. 7 is merely an example, and the display content of the display screen I7 is not limited to this. In one example, the display screen I7 may not display at least one of the PCCT image I71 and the PCCT image I72, and may display, instead, a composite image or the like.

By the above, the progress degree estimation process according to the first embodiment is terminated.

According to the above-described progress degree estimation process, the progress degree of the target tumor can be estimated by using PCCT images relating to the subject to which a plurality of drugs with different particle sizes are administered. Since the progress degree of the target tumor is understood, the progress degree can helpfully be used in formulating a future treatment policy such as a medication treatment or radiation treatment. In addition, according to the present embodiment, since the gap between vascular endothelial cells, which corresponds to the progress degree of the target tumor, can be specified, it becomes possible to appropriately design the particle size of drug particles that are to be delivered to the target tumor. Furthermore, in the present embodiment, since the medical images, in which the spatial distribution of drugs is visualized by PCCT imaging, are collected, the exposure dose can be reduced, compared to ordinary X-ray CT imaging.

The above-described progress degree estimation process is not limited to the above-described processing procedure, and omission, addition and/or modification can freely be made without departing from the spirit of the invention. In one example, although the drugs to be injected into the subject are described as being the drug of particle size "large" and the drug of particle size "small", the sizes of the drugs are not limited to these, and drugs of any particle size may be injected. In addition, the number of kinds of particle sizes is not limited to two, and drugs of three or more kinds of particle sizes may be injected.

In the above-described progress degree estimation process, the processing circuitry 150 is described as estimating the stage of disease as the progress degree, but a TNM classification may be estimated by a similar method. As the TNM classification, a level may be estimated in regard to each of all factors of T, N and M, or a level may be estimated in regard to one or two specific factors.

In another example, although the X-ray CT apparatus 100 is described as executing PCCT imaging, the X-ray CT apparatus 100 may execute single energy CT (SECT) imaging or dual energy CT (DECT) imaging if drugs of different particle sizes can be distinguished. In addition, the processing circuitry 150 may convert a SECT image acquired by SECT imaging, or a DECT image acquired by DECT imaging, into a PCCT image. In one example, this conversion can be executed by using a neural network that is trained to convert a SECT image or a DECT image into a PCCT image. In another example, if a distribution of drugs can be visualized, a magnetic resonance imaging apparatus, an ultrasonic diagnosis apparatus, a PET (Positron Emission Tomography) apparatus, or a SPECT (Single Photon Emission CT) apparatus may be used instead of the X-ray CT apparatus 100.

In another example, although the processing circuitry 150 is described as being provided in the X-ray CT apparatus 100, the processing circuitry 150 may be provided in a PET apparatus 300, or may be provided in a computer (for example, an image processing apparatus) that is different from the X-ray CT apparatus 100.

Applied Example

A medical image diagnosis system 1 according to an applied example uses a vasodilator drug in addition to a drug for contrast-enhancing a cancer tissue. By using the vasodilator drug, the progress degree can be estimated in greater detail. Processing circuitry 150 according to the applied example estimates the progress degree of the target tumor, based on a comparison between a spatial distribution of a drug of a specific particle size among a plurality of drugs on a medical image at a time when the vasodilator drug is not administered to the subject, and a spatial distribution of the drug of the specific particle size on a medical image at a time when the vasodilator drug is administered to the subject. Hereinafter, the medical image diagnosis system 1 according to the applied example is described. In the description below, structural elements having substantially the same functions as in the first embodiment are denoted by like reference signs, and an overlapping description is given only where necessary.

The vasodilator drug according to the applied example has an effect of dilating a gap between vascular endothelial cells by dilating a blood vessel. By dilating the gap between vascular endothelial cells, extravascular leakage of drug particles in the blood vessel is promoted. In one example, as the vasodilator drug, use can be made of a spontaneous carbon monoxide releasing drug (NOC-18) sealed in a liposome. By the administration of the spontaneous carbon monoxide releasing drug, the liposome is absorbed in the cancer tissue by the EPR effect, and then carbon monoxide (NO) is gradually released and induces vasodilation. In another example, as the vasodilator drug, use can be made of serum albumin in which S-Nitrosothiol for achieving local vasodilation is incorporated.

Figure 8:
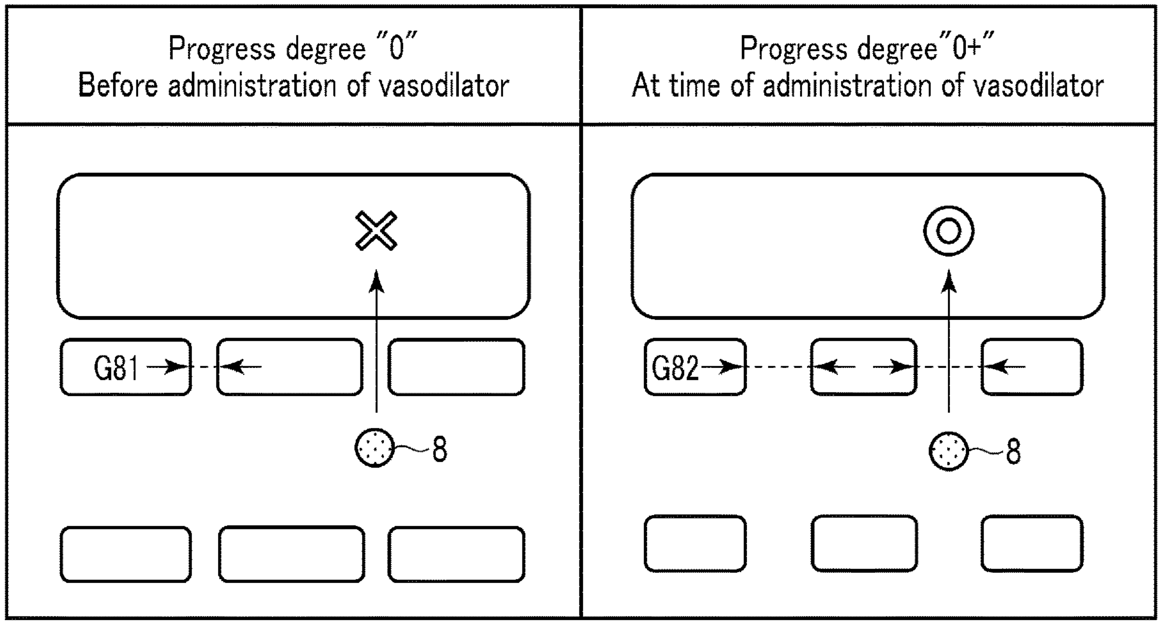
FIG. 8 is a diagram illustrating a relationship between the presence/absence of administration of a vasodilator drug and a progress degree.

FIG. 8 is a diagram illustrating a relationship between the presence/absence of administration of a vasodilator drug and a progress degree. As illustrated in FIG. 8, it is assumed that the target tumor is cancer, which is in an early stage and is classified into a progress degree "0". It is assumed that the gap between vascular endothelial cells, which corresponds to the progress degree "0", is G81. It is assumed that the gap of a blood vessel that feeds the cancer in the early stage is dilated to G82 by the vasodilator drug. It is assumed that the gap G82 is wider than a gap G83 (not illustrated in FIG. 8) of a blood vessel that feeds a normal tissue, which is dilated by the vasodilator drug. It is assumed that a drug 8 cannot pass through the gaps G81 and G83, but can pass through the gap G82.

Before the administration of the vasodilator drug, since the blood vessel does not dilate, the gap between vascular endothelial cells is the gap G81, and the drug 8 cannot pass through the gap G81. Here, by administering the vasodilator drug, vasodilation is induced, and the gap dilates from G81 to G82. Accordingly, after the administration of the vasodilator drug, the drug 8 passes through the gap G82, and accumulates in the target tumor.

The processing circuitry 150 according to the applied example estimates the progress degree of the target tumor, based on the comparison between the spatial distributions of the drug of the specific particle size before and after the administration of the vasodilator drug. In the case of the example of FIG. 8, the imaging apparatus 110 executes PCCT imaging at a time after the injection of the drug 8 and before the administration of the vasodilator drug, and reconstructs the PCCT image representing the spatial distribution of the drug 8. As the PCCT imaging, K-edge imaging utilizing the K-edge of the drug 8 may preferably be executed. In addition, the imaging apparatus 110 executes PCCT imaging at a time after the injection of the drug 8 and after the administration of the vasodilator drug, and reconstructs the PCCT image representing the spatial distribution of the drug 8. As the PCCT imaging, too, K-edge imaging utilizing the K-edge of the drug 8 may preferably be executed. Since there is no need to visualize the vasodilator drug, there is no need to execute K-edge imaging on the vasodilator drug as the target.

The processing circuitry 150 determines whether the drug accumulates in the target tumor on the PCCT image before the administration of the vasodilator drug. If the drug accumulates in the target tumor, the processing circuitry 150 determines that the progress degree is "1". If the drug does not accumulate in the target tumor, the processing circuitry 150 compares the PCCT image before the administration of the vasodilator drug and the PCCT image after the administration of the vasodilator drug, and determines whether the drug accumulates in the target tumor, with respect to only the PCCT image after the administration of the vasodilator drug. Specifically, the processing circuitry 150 generates a difference image between the PCCT image before the administration of the vasodilator drug and the PCCT image after the administration of the vasodilator drug, and if the drug accumulates in the target tumor on the difference image, the processing circuitry 150 determines that the drug accumulates in the target tumor, with respect to only the PCCT image after the administration of the vasodilator drug. In this case, although the target tumor is suspected to be cancer, this means that the progress degree is less than "1". Accordingly, the processing circuitry 150 estimates that the progress degree is "0+". "0+" means an intermediate between "0" and "1". On the other hand, if the drug does not accumulate in the target tumor on the difference image, the processing circuitry 150 estimates that the progress degree is "0". The estimation result of the progress degree is displayed on the display device 170.

According to the applied example, by comparing the spatial distributions of a drug of a specific particle size before and after the administration of a vasodilator drug, a detailed progress degree can be estimated, compared to the case where the vasodilator drug is not used. In particular, even in such a case where cancer is present but the gap between vascular endothelial cells is still narrow, the presence of cancer can be detected at an early stage.

Second Embodiment

In the above first embodiment, the tumor characteristic is described as being the progress degree. It is assumed that a tumor characteristic according to a second embodiment is a tumor type. The tumor type means a pathological classification of a tumor, such as whether a primary focus or not, whether a metastasis focus or not, whether benign or not, or the like. In this case, a plurality of drugs have a tumor type sensitivity as a tumor accumulation property. The tumor type sensitivity of the drug means the ease with which the drug is taken in the target tumor in accordance with the tumor type. Hereinafter, a medical image diagnosis system 2 according to the second embodiment is described. In the description below, structural elements having substantially the same functions as in the first embodiment are denoted by like reference signs, and an overlapping description is given only where necessary.

Figure 9:
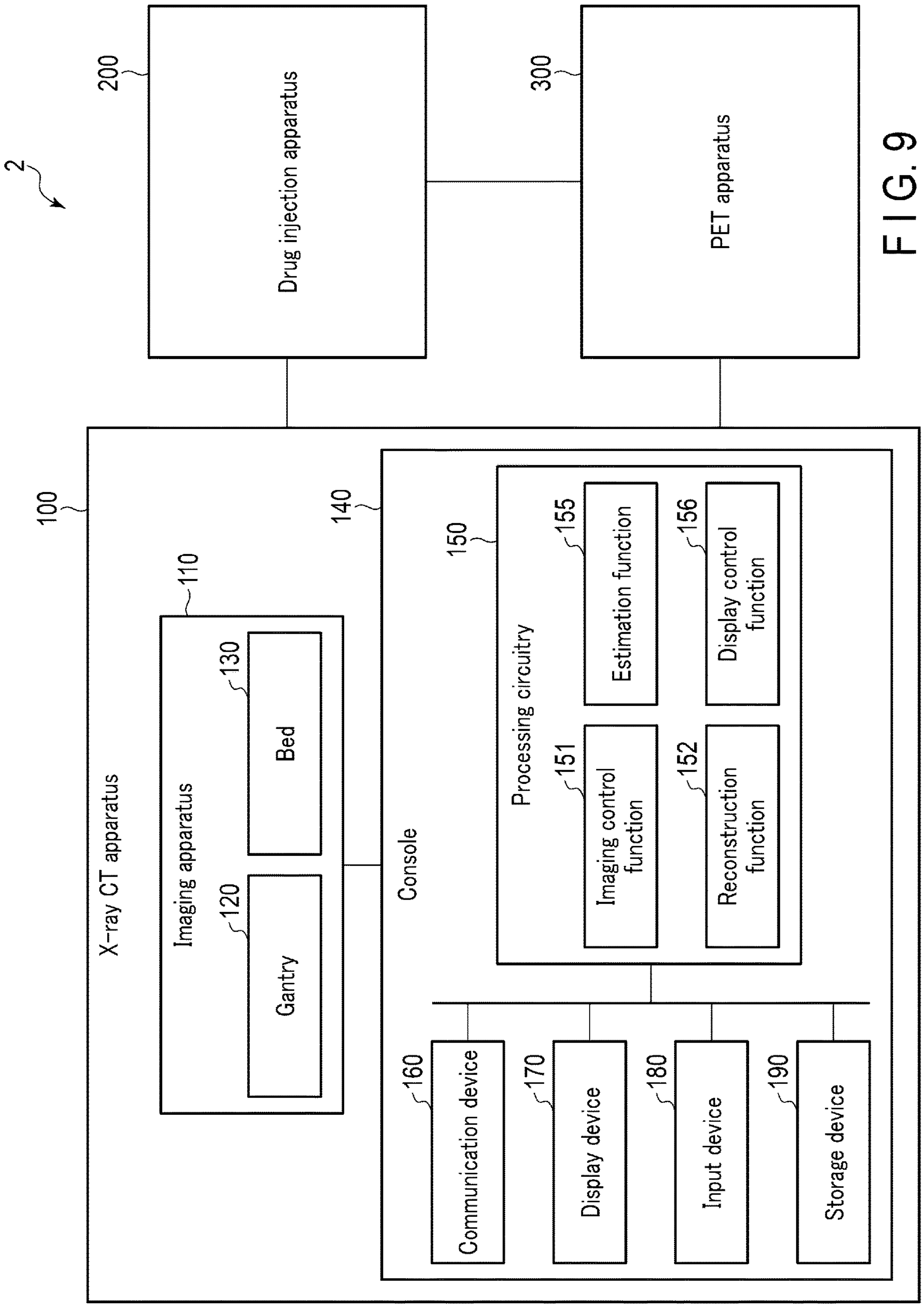
FIG. 9 is a diagram illustrating a configuration example of a medical image diagnosis system according to a second embodiment.

FIG. 9 is a diagram illustrating a configuration example of the medical image diagnosis system 2 according to the second embodiment. As illustrated in FIG. 9, the medical image diagnosis system 2 includes an X-ray CT apparatus 100, a drug injection apparatus 200, and a PET apparatus 300. The X-ray CT apparatus 100, drug injection apparatus

200 and PET apparatus 300 are connected to be capable of mutually communicating information.

The PET apparatus 300 detects, by a gamma ray detector, a pair of gamma rays emitted from the body of the subject to which a PET drug is administered. The PET drug includes glucose, and a radioactive isotope that is attached to the glucose and emits a positron. A cancer cell takes in a greater amount of glucose than a normal cell. If the PET drug is administered to the subject, a large amount of the PET drug is taken in the cancer cell. A positron is emitted from the radioactive isotope included in the taken-in PET drug, and pair annihilation occurs with a nearby electron. In accordance with the pair annihilation, a pair of gamma rays of 511 keV occur at about 180 degrees. The gamma ray detector detects the generated gamma rays. Based on the energy and detection position information of the detected gamma rays, the PET apparatus 300 generates a PET image representing the spatial distribution of the PET drug or radioactive isotope. As described above, since a large amount of the PET drug is taken in the cancer cell, the PET image can be expressed as an image in which the distribution of cancer cells in the body of the subject is visualized. The data of the PET image is supplied to the X-ray CT apparatus 100.

By implementing an estimation function 155, the processing circuitry 150 according to the second embodiment estimates the tumor type of the target tumor included in the subject, based on the spatial distribution of a plurality of drugs, which is rendered on one or a plurality of PCCT images. In the second embodiment, a first drug among a plurality of drugs accumulates in tumors of a plurality of tumor types, and a second drug accumulates in a tumor of a specific tumor type among the tumor types. The processing circuitry 150 estimates the tumor type, based on a difference between the spatial distribution of the first drug, which is rendered on a first medical image at a time when the first drug is administered to the subject, and the spatial distribution of the second drug, which is rendered on a second medical image at a time when the second drug is administered to the subject. In one example, the first drug is a PET drug used for PET imaging, and the second drug is a drug used for PCCT imaging. Specifically, the first medical image is a PET image, and the second medical image is a PCCT image.

By implementing a display control function 156, the processing circuitry 150 displays various information on the display device 170. In one example, the processing circuitry 150 displays a PET image, a PCCT image, a tumor type, and the like.

Figure 10:
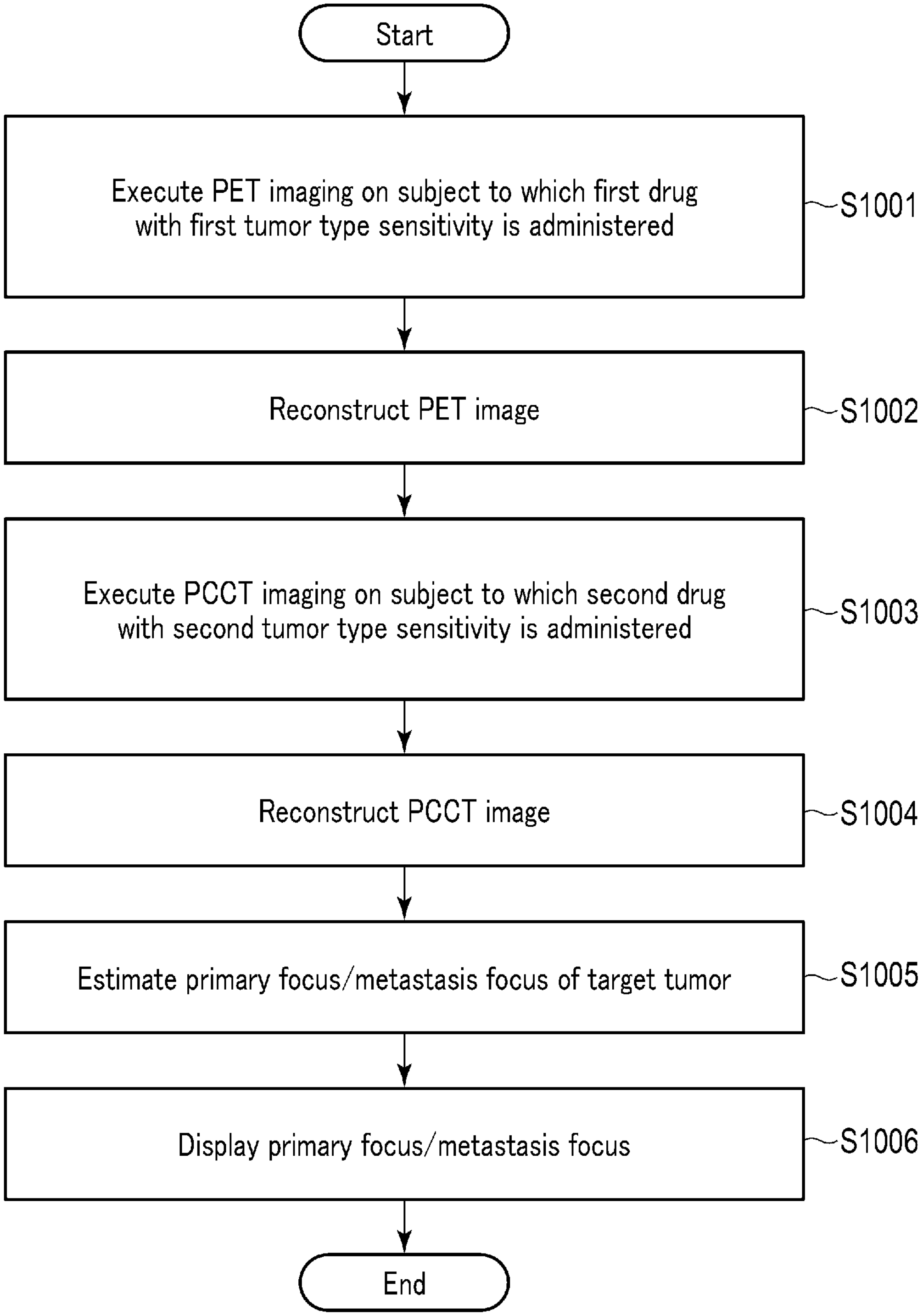
FIG. 10 is a flowchart illustrating a processing procedure relating to a tumor type estimation process according to the second embodiment.
Figure 11:
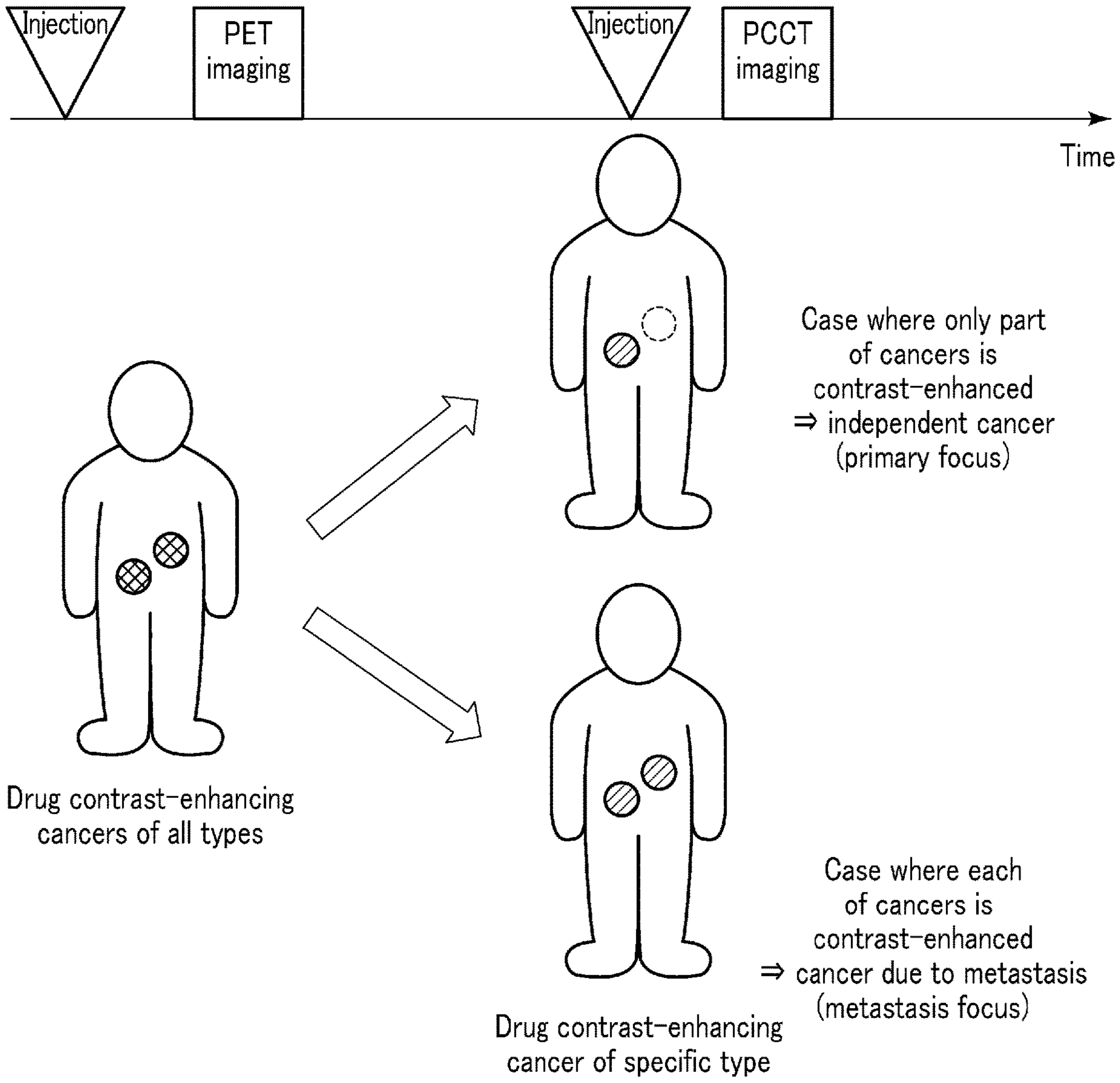
FIG. 11 is a timing chart of drug injection and medical imaging in the tumor type estimation process.

FIG. 10 is a flowchart illustrating a processing procedure relating to a tumor type estimation process according to the second embodiment. It is assumed that the tumor types in the embodiment below are a primary focus and a metastasis focus. FIG. 11 is a timing chart of drug injection and medical imaging in the tumor type estimation process. In FIG. 10 and FIG. 11, a clinical example is assumed in which a medication treatment of cancer is performed while executing medical imaging and performing follow-up observation of cancer.

As illustrated in FIG. 10, by implementing the imaging control function 151, the PET apparatus 300 executes PET imaging on the subject to which the first drug (PET drug) having a first tumor type sensitivity is administered (step S1001). As illustrated in FIG. 11, to begin with, the PET drug is injected in the subject by the drug injection apparatus 200. The PET drug has sensitivity to all types of cancers. Specifically, the PET drug performs contrast-enhancement relating to whether each cancer tissue is a primary focus or a metastasis focus. If the PET drug is injected, the PET apparatus 300 executes PET imaging on the subject.

If step S1001 is executed, the PET apparatus 300 reconstructs the PET image, based on the gamma ray detection data collected by the PET imaging executed in step S1001 (step S1002). On the PET image, all types of cancer existing in the subject are rendered.

If step S1002 is executed, the X-ray CT apparatus 100 executes PCCT imaging on the subject to which the second drug having a second tumor type sensitivity is administered (step S1003). As illustrated in FIG. 11, in step S1003, to begin with, the second drug (PCCT drug) is injected in the subject by the drug injection apparatus 200. As the PCCT drug, an anticancer drug labeled with a high atomic number substance is used. The anticancer drug is taken into only a primary focus that is a target, or a metastasis focus of the primary focus. Preferably, as the PCCT imaging, use is made of K-edge imaging utilizing the K-edge of the high atomic number substance that is a label substance.

As illustrated in FIG. 11, a case is now considered in which cancer tissues, for example, liver cancer and stomach cancer, are present at two locations of the subject. In a case where the stomach cancer and the liver cancer are mutually independent primary focuses, if a PCCT drug including an anticancer drug for treating the liver cancer is injected, the PCCT drug is taken in the liver cancer, but is not taken in the stomach cancer. In other words, in a case where only a part of a plurality of cancers contrast-enhanced by the PET drug is contrast-enhanced by the PCCT drug, it can be said that the contrast-enhanced cancer and the non-contrast-enhanced cancer are mutually different primacy focuses.

On the other hand, in a case where the stomach cancer is a metastasis focus of the liver cancer, if the PCCT drug including an anticancer drug for treating the liver cancer is injected, the PCCT drug is taken into not only the liver cancer but also the stomach cancer. In other words, in a case where all of a plurality of cancers contrast-enhanced by the PET drug are contrast-enhanced by the PCCT drug, it can be said that these cancers have a relationship of a primary focus and a metastasis focus. To be more specific, it can be estimated that the cancer of a region that is the target of the anticancer drug included in the injected PCCT drug is a primary focus, and the cancer of another region is a metastasis focus.

If step S1003 is executed, the X-ray CT apparatus 100 reconstructs the PCCT image (step S1004). In step S1004, by implementing the reconstruction function 152, the processing circuitry 150 reconstructs a PCCT image representing the spatial distribution of count numbers of the PCCT drug, based on the spectral data collected by the PCCT imaging (K-edge imaging) in step S1003.

If step S1004 is executed, the X-ray CT apparatus 100 estimates the tumor type (primary focus or metastasis focus) of the target tumor (step S1005). In step S1005, by implementing the estimation function 155, the processing circuitry 150 estimates the tumor type (primary focus or metastasis focus) of each target tumor, based on a difference between the spatial distribution of the PET drug, which is rendered by the PET image reconstructed in step S1002, and the spatial distribution of the PCCT drug, which is rendered by the PCCT image reconstructed in step S1004. Specifically, the processing circuitry 150 specifies a cancer area from the PET image, based on the spatial distribution of the PET drug. As described above, in the PET image, all cancers included in the subject are visualized. Similarly, the processing circuitry 150 specifies a cancer area from the PCCT image, based on the spatial distribution of the PCCT drug.

In the PCCT image, only the cancer, which is the target of the anticancer drug included in the injected PCCT drug, or the metastasis focus of the cancer, is visualized.

Next, the processing circuitry 150 compares the PET image and the PCCT image, and, if a cancer area is present at the same part of both images, the processing circuitry 150 estimates that the cancer type corresponding to the cancer area is a primary focus. On the other hand, if there is a cancer area that is not included in the PCCT image but is included in the PET image, the processing circuitry 150 estimates that the cancer type corresponding to the cancer area is a metastasis focus.

If step S1005 is executed, the X-ray CT apparatus 100 displays the tumor type (primary focus or metastasis focus) estimated in step S1005 (step S1006). In step S1006, by implementing the display control function 156, the processing circuitry 150 displays the tumor type on the display device 170 with a freely selected layout.

Figure 12:
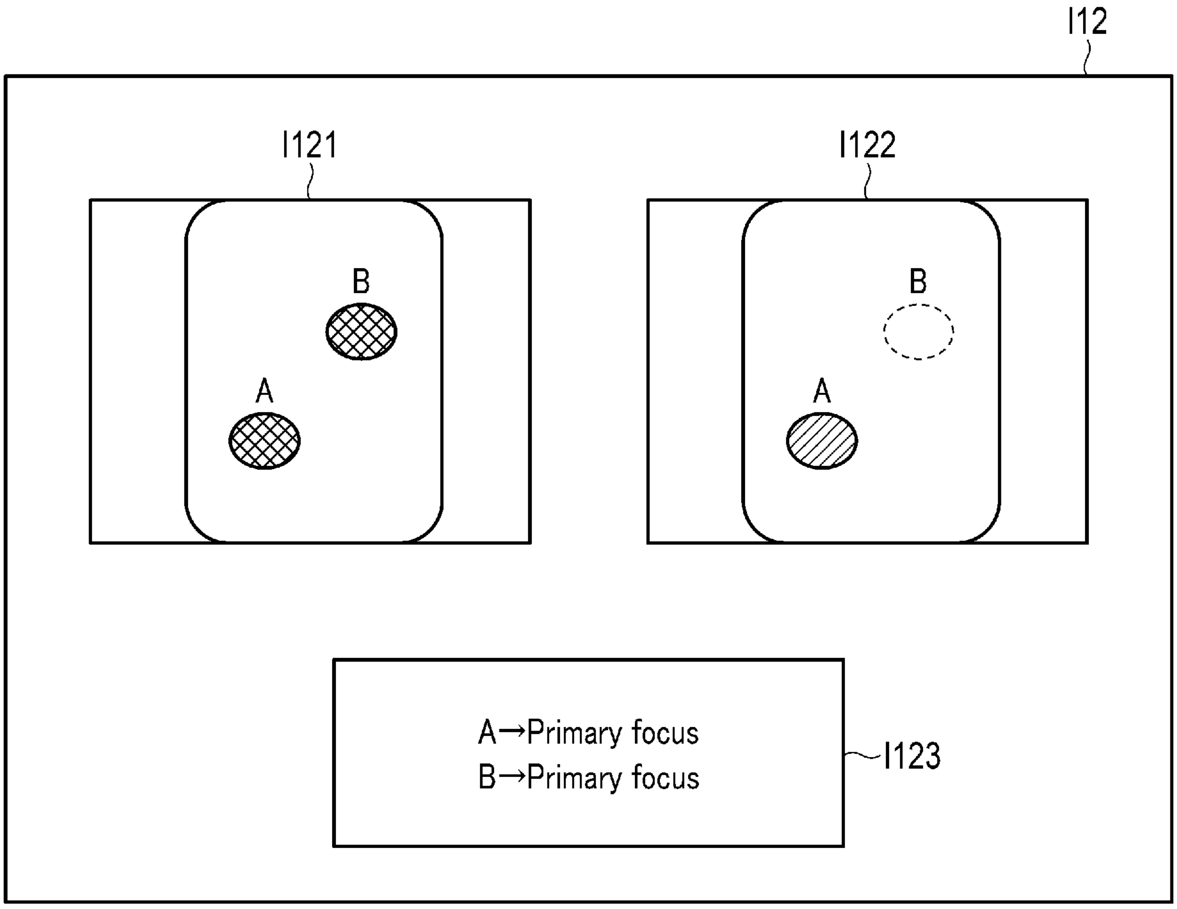
FIG. 12 is a diagram exemplarily illustrating a display screen of a tumor type.

FIG. 12 is a diagram exemplarily illustrating a display screen I12 of a tumor type. As illustrated in FIG. 12, the display screen I12 displays a PET image I121, a PCCT image I122, and a display field I123 of the tumor type. In one example, cancer A and cancer B, which are contrast-enhanced by the PET drug, are rendered on the PET image I121. Labels of cancer, such as "A" and "B", may be displayed on the PET image I121 and PCCT image I122. In the PCCT image I122, the cancer A, which is contrast-enhanced by the PCCT drug, is rendered, but the cancer area B, which is not contrast-enhanced by the PCCT drug, is not rendered. In this case, the cancer A and the cancer B are estimated to be different primary focuses. The display field I123 displays a message relating to the tumor type, which indicates that the cancer A and the cancer B are primary focuses.

As illustrated in FIG. 12, since the tumor type, the PET image I121 and the PCCT image I122 are displayed in an arranged manner, the worker can evaluate the reliability of the tumor type by confirming the PET image I121 and PCCT image I122. In addition, in a case where the type of a primary focus, i.e., the region of occurrence of the primary focus, can be estimated, the region of occurrence may be displayed in the display field I123 or the like. Similarly, in a case where the type of a metastasis focus, i.e., the region of occurrence of the metastasis focus, can be estimated, the region of occurrence may be displayed in the display field I123 or the like.

Note that the display screen I12 illustrated in FIG. 12 is merely an example, and the display content of the display screen I12 is not limited to this. In one example, at least one of the PET image I121 and the PCCT image I122 may not be displayed on the display screen I12.

By the above, the tumor type estimation process according to the second embodiment is completed.

According to the above-described tumor type estimation process, the tumor type (primary focus/metastasis focus) can be estimated by using the PET image and PCCT image relating to the subject to which drugs with mutually different tumor type sensitivities are administered. Here, by executing not only PCCT imaging but also PET imaging, the exposure dose of the subject can be reduced, compared to entirely executing PCCT imaging. In addition, by including the anticancer drug in the PCCT drug, the tumor type can be estimated while a medication treatment is being performed. By estimating the tumor type, a future anticancer drug treatment can effectively be performed. For example, according to the above-described process, even in a case where only a liver cancer and a metastasis focus thereof were considered to be present in a subject, it can be understood that a primary focus in another primary focus region is present. It is thus possible to be aware that an anticancer drug that is effective to the cancer of the another primary focus region should be used. In other words, an optimal anticancer drug for the subject can individually be selected, and, by extension, the medication treatment can effectively be performed. Furthermore, since the amount of the anticancer drug to be used can be reduced, it is expected that side effects can also be reduced.

The above-described tumor type estimation process is not limited to the above-described processing procedure, and omission, addition and/or modification can freely be made without departing from the spirit of the invention. If cancers of all tumor types can be contrast-enhanced by the PCCT drug, PCCT imaging may be executed instead of PET imaging. In this case, it is preferable that the first drug includes an iodine preparation that contrast-enhances tumors of a plurality of types, and the second drug includes an anticancer drug for a tumor of a specific type. Note that in a case where the image quality of an anticancer drug on the PCCT image is poor, the anticancer drug may be labeled with a high atomic number substance. In addition, since it suffices that a drug accumulating in cancer is visualized, if such a drug is present, a magnetic resonance imaging apparatus, an ultrasonic diagnosis apparatus, a PET apparatus, or a SPECT apparatus may be used instead of the X-ray CT apparatus 100.

In another example, although the X-ray CT apparatus 100 is described as executing PCCT imaging, the X-ray CT apparatus 100 may execute SECT imaging or DECT imaging if drugs of different particle sizes can be distinguished. In addition, the processing circuitry 150 may convert a SECT image acquired by SECT imaging, or a DECT image acquired by DECT imaging, into a PCCT image. In one example, this conversion can be executed by using a neural network that is trained to convert a SECT image or a DECT image into a PCCT image.

In another example, although the processing circuitry 150 is described as being provided in the X-ray CT apparatus 100, the processing circuitry 150 may be provided in the PET apparatus 300, or may be provided in a computer (for example, an image processing apparatus) that is different from the X-ray CT apparatus 100 and the PET apparatus 300.

CONCLUSION

According to the above-described various embodiments, the medical image diagnosis system 1, 2 includes an imaging unit, a reconstruction unit, an estimation unit, and a display control unit. The imaging unit applies one-time or multiple-time medical imaging to a subject to which a plurality of drugs having a tissue accumulation property, which corresponds to a tissue characteristic, are administered successively or simultaneously. The reconstruction unit reconstructs one or a plurality of medical images, based on one or a plurality of set of raw data acquired by the one-time or multiple-time medical imaging. The estimation unit estimates a tissue characteristic of a target region included in the subject, based on a spatial distribution of the drugs rendered on the one or the plurality of medical images. The display control unit displays the estimated tissue characteristic on a display device.

In the case of the first embodiment, the imaging unit corresponds to the imaging apparatus 110 of the X-ray CT apparatus 100, and the reconstruction unit, estimation unit and display control unit correspond to the processing circuitry 150. In the case of the second embodiment, the imaging unit corresponds to the imaging apparatus 110 of the X-ray CT apparatus 100 and the PET apparatus 300, and the reconstruction unit, estimation unit and display control unit correspond to the processing circuitry 150 of the X-ray CT apparatus 100.

According to the above-described configuration, the tissue characteristic can be estimated from the spatial distribution of the drugs, by utilizing the relationship between the tissue characteristic and the tissue accumulation property. Since it suffices that drug injection and medical imaging are executed for the subject, the tissue characteristic can be estimated by means with a small load on the subject. In addition, by estimating the tissue characteristic, a future treatment policy can appropriately be formulated. For example, at a time point when the tissue characteristic of the target region is estimated, the tissue accumulation property for the target region is already known, and it is thus possible to helpfully use this in designing drugs that are administered to the target region.

In the above-described first embodiment and second embodiment, it is assumed that the target region is a tumor, or a tissue that is suspected to be a tumor. In addition, it is assumed that the tissue characteristic is the progress degree or type of a tumor, and the tissue accumulation property is a capability of accumulation of a drug in a tumor. However, the present embodiment is not limited to this. Specifically, the target region is not limited to a tumor or the like, and may be any tissue if the target region is a biological tissue having such a property as accumulating a drug. Accordingly, the tissue characteristic may be the progress degree of mutation or the type of a target tissue, and the tissue accumulation property may be such a capability that a drug accumulates in the target tissue. In addition, the tumor type sensitivity according to the second embodiment means the ease with which the drug is taken in the target tissue in accordance with the tissue type. It is assumed that the tissue type includes any pathological classification, as well as a classification of a malignancy degree, such as whether benign or malignant.

According to at least one of the above-described embodiments, the characteristic of a tissue, in which a drug accumulates, can appropriately be determined.

The term "processor" used in the above description means, for example, circuitry such as a CPU, a GPU, an application specific integrated circuit (ASIC), or a programmable logic device (for example, a simple programmable logic device (SPLD), a complex programmable logic device (CPLD) or a field programmable gate array (FPGA)). The processor implements functions by reading and executing a program stored in the storage circuitry. Note that, instead of storing the program in the storage circuitry, such a configuration may be adopted that the program is directly assembled in the circuitry of the processor. In this case, the processor implements functions by reading and executing the program assembled in the circuitry of the processor. On the other hand, in a case where the processor is, for example, an ASIC, the functions are directly assembled as logic circuitry in the circuitry of the processor, instead of the program being stored in the storage circuitry. Note that the processors in the embodiments are not limited to cases where each processor is constituted as single circuitry, and a plurality of independent circuities may be combined to constitute one processor and to implement functions thereof. Furthermore, a plurality of constituent elements in FIG. 1 and FIG. 9 may be integrated into one processor, and the processor may implement the functions thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis system comprising:

an imaging apparatus configured to apply one-time or multiple-time medical imaging to a subject to which a plurality of drugs having a tissue accumulation property, which corresponds to a tissue characteristic, are administered successively or simultaneously, wherein the drugs have mutually different particle sizes; and processing circuitry configured to:

reconstruct one or a plurality of medical images, based on one or a plurality of set of raw data acquired by the one-time or multiple-time medical imaging;

estimate a tissue characteristic of a target region included in the subject, based on a spatial distribution of the drugs rendered on the one or the plurality of medical images;

estimate a progress degree of the target region as the tissue characteristic;

estimate that the progress degree is a first progress degree, in a case where only a drug of a first particle size, among the drugs, is distributed in the target region on the one or the plurality of medical images;

estimate that the progress degree is a second progress degree that is more advanced than the first progress degree, in a case where a drug of a second particle size greater than the first particle size, among the drugs, is distributed in the target region on the one or the plurality of medical images; and display the estimated tissue characteristic on a display device.

2. The medical image diagnosis system of claim 1, wherein the processing circuitry is further configured to estimate that the progress degree is a third progress degree that is less advanced than the first progress degree, in a case where each of the drug of the first particle size and the drug of the second particle size is distributed in the target region.

3. The medical image diagnosis system of claim 1, wherein the processing circuitry is further configured to estimate the progress degree of the target region, based on a comparison between a spatial distribution of a drug of a specific particle size among the drugs on the medical image at a time when a vasodilator drug is not administered to the subject, and a spatial distribution of the drug of the specific particle size on a medical image at a time when the vasodilator drug is administered to the subject.

4. The medical image diagnosis system of claim 1, wherein the plurality of drugs are labeled with mutually different heavy metals, and the imaging apparatus is further configured to execute, as the one-time or multiple-time medical imaging, K-edge imaging for targets that are the heavy metals included in the drugs.

5. The medical image diagnosis system of claim 1, wherein the target region is a tumor, or a tissue that is suspected to be a tumor, the tissue characteristic is a tumor type that means a progress degree or a type of a tumor, and the tissue accumulation property is a capability of accumulation of a drug in a tumor.

6. The medical image diagnosis system of claim 5, wherein the processing circuitry is further configured to estimate a TNM classification as the tumor characteristic.

7. A medical image diagnosis system comprising:

an imaging apparatus configured to apply one-time or multiple-time medical imaging to a subject to which a plurality of drugs having a tissue accumulation property, which corresponds to a tissue characteristic, are administered successively or simultaneously, wherein the drugs have mutually different tissue type sensitivities, a first drug among the drugs accumulates in tissues of a plurality of types, a second drug among the drugs accumulates in a tissue of a specific type among the types; and processing circuitry configured to:

reconstruct one or a plurality of medical images, based on one or a plurality of set of raw data acquired by the one-time or multiple-time medical imaging;

estimate a tissue characteristic of a target region included in the subject, based on a spatial distribution of the drugs rendered on the one or the plurality of medical images;

estimate a tissue type of the target region as the tissue characteristic;

estimate the tissue type as the tissue characteristic, based on a difference between a spatial distribution of the first drug rendered on a first medical image at a time when the first drug is administered to the subject, and a spatial distribution of the second drug rendered on a second medical image at a time when the second drug is administered to the subject;

estimate that cancers have a relationship of a primary focus and a metastasis focus in a case where all of a plurality of cancers contrast-enhanced by the first drug are contrast-enhanced by the second drug;

estimate that a contrast-enhanced cancer and a non-contrast-enhanced cancer are mutually different primary focuses in a case where only a part of the plurality of cancers contrast-enhanced by the first drug is contrast-enhanced by the second drug; and display the estimated tissue characteristic on a display device, wherein the target region is a tumor, or a tissue that is suspected to be a tumor, the tissue characteristic is a tumor type that means a progress degree or a type of a tumor, the tissue accumulation property is a capability of accumulation of a drug in a tumor, and the tumor type includes a primary focus and a metastasis focus.

8. The medical image diagnosis system of claim 7, wherein the first drug is a contrast agent used in PET imaging that contrast-enhances the tissues of the plurality of types, and the second drug is a contrast agent used in PCCT imaging that contrast-enhances the tissue of the specific type.

9. The medical image diagnosis system of claim 7, wherein the target region is a tumor, or a tissue that is suspected to be a tumor, the tissue characteristic is a tumor type that means a progress degree or a type of a tumor, the tissue accumulation property is a capability of accumulation of a drug in a tumor, the first drug includes an iodine preparation that contrast-enhances tumors of the plurality of types, and the second drug includes an anticancer drug for a tumor of the specific type.

10. A medical image diagnosis method comprising:

applying one-time or multiple-time medical imaging to a subject to which a plurality of drugs having a tissue accumulation property, which corresponds to a tissue characteristic, are administered successively or simultaneously, wherein the drugs have mutually different particle sizes;

reconstructing one or a plurality of medical images, based on one or a plurality of set of raw data acquired by the one-time or multiple-time medical imaging;

estimating a tissue characteristic of a target region included in the subject, based on a spatial distribution of the drugs rendered on the one or the plurality of medical images;

estimating a progress degree of the target region as the tissue characteristic;

estimating that the progress degree is a first progress degree, in a case where only a drug of a first particle size, among the drugs, is distributed in the target region on the one or the plurality of medical images;

estimating that the progress degree is a second progress degree that is more advanced than the first progress degree, in a case where a drug of a second particle size greater than the first particle size, among the drugs, is distributed in the target region on the one or the plurality of medical images; and displaying the estimated tissue characteristic on a display device.

11. A medical image diagnosis method comprising:

applying one-time or multiple-time medical imaging to a subject to which a plurality of drugs having a tissue accumulation property, which corresponds to a tissue characteristic, are administered successively or simultaneously, wherein the drugs have mutually different tissue type sensitivities, a first drug among the drugs accumulates in tissues of a plurality of types, a second drug among the drugs accumulates in a tissue of a specific type among the types;

reconstructing one or a plurality of medical images, based on one or a plurality of set of raw data acquired by the one-time or multiple-time medical imaging;

estimating a tissue characteristic of a target region included in the subject, based on a spatial distribution of the drugs rendered on the one or the plurality of medical images;

estimating a tissue type of the target region as the tissue characteristic;

estimating the tissue type as the tissue characteristic, based on a difference between a spatial distribution of the first drug rendered on a first medical image at a time when the first drug is administered to the subject, and a spatial distribution of the second drug rendered on a second medical image at a time when the second drug is administered to the subject;

estimating that cancers have a relationship of a primary focus and a metastasis focus in a case where all of a plurality of cancers contrast-enhanced by the first drug are contrast-enhanced by the second drug;

estimating that a contrast-enhanced cancer and a non-contrast-enhanced cancer are mutually different primary focuses in a case where only a part of the plurality of cancers contrast-enhanced by the first drug is contrast-enhanced by the second drug; and displaying the estimated tissue characteristic on a display device, wherein the target region is a tumor, or a tissue that is suspected to be a tumor, the tissue characteristic is a tumor type that means a progress degree or a type of a tumor, the tissue accumulation property is a capability of accumulation of a drug in a tumor, and the tumor type includes a primary focus and a metastasis focus.

* * * * *